United States Patent
Hsieh et al.

(10) Patent No.: US 11,612,171 B2
(45) Date of Patent: Mar. 28, 2023

(54) FOOD COMPOSITION AND PHARMACEUTICAL COMPOSITION WITH STRAINS OF LACTIC ACID BACTERIA AND METHOD FOR MODULATING BLOOD GLUCOSE

(71) Applicant: GLAC BIOTECH CO., LTD., Tainan (TW)

(72) Inventors: Pei-Shan Hsieh, Tainan (TW); Chung-Wei Kuo, Tainan (TW); Yi-Chun Tsai, Tainan (TW); Hsieh-Hsun Ho, Tainan (TW); Yi Wei Kuo, Tainan (TW)

(73) Assignee: GLAC BIOTECH CO., LTD., Tainan (TW)

( * ) Notice: Subject to any disclaimer, the term of this patent is extended or adjusted under 35 U.S.C. 154(b) by 500 days.

(21) Appl. No.: 16/599,496

(22) Filed: Oct. 11, 2019

(65) Prior Publication Data

US 2020/0390119 A1    Dec. 17, 2020

(30) Foreign Application Priority Data

Jun. 14, 2019   (TW) .................................. 108120798

(51) Int. Cl.
| | | |
|---|---|---|
| *A23C 9/123* | (2006.01) | |
| *A23C 19/032* | (2006.01) | |
| *A23C 19/06* | (2006.01) | |
| *A61P 3/10* | (2006.01) | |
| *A61K 35/747* | (2015.01) | |

(52) U.S. Cl.
CPC ........ *A23C 9/1232* (2013.01); *A23C 19/0323* (2013.01); *A23C 19/062* (2013.01); *A61K 35/747* (2013.01); *A61P 3/10* (2018.01); *A23Y 2220/71* (2013.01); *A23Y 2220/79* (2013.01)

(58) Field of Classification Search
None
See application file for complete search history.

(56) References Cited

U.S. PATENT DOCUMENTS

2011/0268715 A1*   11/2011   Hsieh ..................... A23L 33/135
424/93.45

FOREIGN PATENT DOCUMENTS

CN           106852939 A  *  6/2017

* cited by examiner

*Primary Examiner* — Robert J Yamasaki
*Assistant Examiner* — Charles Zoltan Constantine
(74) *Attorney, Agent, or Firm* — Locke Lord LLP; Tim Tingkang Xia, Esq.

(57) ABSTRACT

A food composition and pharmaceutical composition with strains of lactic acid bacteria for modulating blood glucose are provided, comprising an isolated lactic acid bacteria strain. The isolated lactic acid bacteria strain is at least one selected from a group including a GL-104 strain of *Lactobacillus reuteri* (CCTCC NO: M209138), an AP-32 strain of *Lactobacillus salivarius* subsp. *salicinius* (CCTCC NO: M2011127), a TYCA06 strain of *Lactobacillus acidophilus* (CGMCC No: 15210), and an MH-68 strain of *Lactobacillus johnsonii* (CCTCC NO: M2011128), or a combination thereof.

9 Claims, 4 Drawing Sheets

FOOD COMPOSITION AND PHARMACEUTICAL COMPOSITION WITH STRAINS OF LACTIC ACID BACTERIA AND METHOD FOR MODULATING BLOOD GLUCOSE

BACKGROUND OF THE INVENTION

1. Field of the Invention

The present invention relates to food compositions and pharmaceutical compositions, particularly to food compositions, pharmaceutical compositions with lactic acid bacteria strains and method for modulating blood glucose.

2. Description of the Prior Art

Owing to variation in the style of diet and living, metabolism syndromes have become prevailing diseases. For example, high blood glucose may lead to diabetes. Diabetes is a disease related with persistent metabolic disorders. Diabetes may cause some complications, such as cardiovascular diseases, apoplexy, blindness, renal failure, and Alzheimer's disease. Therefore, we should pay more attention to prevention and treatment of hyperglycemia.

Traditionally, oral antidiabetic drugs are used to treat hyperglycemia. There are six groups of antidiabetic drugs usually used to treat hyperglycemia, including (1) the sulfonylurea group, such as Amaryl, Glibenclamide, Minidiab, and Diamicron; (2) the biguanide group, such as Glucophage; (3) the thiazolidinedione(TZD) group, such as Actos and Avandia; (4) the Meglitinides group, such as Novonorm and Starlix; (5) the α-Glucosidase inhibitor group, such as Glucobay; (6) the Dipeptidyl peptidase 4 (DPP-4) inhibitor group, such as Januvia.

However, the oral antidiabetic drugs usually have the side effects of hypoglycemia or gastrointestinal disorders. Besides, these drugs will fail to work after long-term use. Thus, the patients will be forced to accept insulin injection. Measuring blood glucose and injecting insulin every day should greatly degrade the quality of life. Therefore, it is an urgency to develop a convenient and safe nutritional supplement having fewer side effects and able to modulate blood glucose in the long term.

So far, only few strains have been experimentally confirmed to have the effect of modulating blood glucose. The functionality of lactic acid bacteria to health is not based on the species of bacteria but dependent on the specificities of strains (Guidelines for the evaluation of probiotics in food; Report of joint FAO/WHO working group on drafting guidelines for the evaluation of probiotics in food; London Ontario, Canada Apr. 30 and May 1, 2002: 1-7). In the paper published by Singh, et al. in 2017 (Beneficial Microbes, 2017; 8(2): 243-255), the author fed the mice suffering from Type 2 diabetes with *Lactobacillus rhamnosus* to test whether the lactic acid bacterium can improve diabetes, wherein 6 weeks later after the mice were fed with the NCDC 17 strain and LGG strain, an oral glucose tolerance test (OGTT) was undertaken. The experimental results show that the NCDC 17 strain is much superior to the LGG strain in blood glucose modulating capability. Besides, there is significant difference between the fasting blood glucose control abilities of the two strains. Further, it is the NCDC 17 strain but not the LGG strain that has the effects of controlling insulin, glycohemoglobin, triacylglycerol, and cholesterol in blood. The phenomenon indicates that the ability of improving diabetes is strain-specific although these strains belong to the same lactic acid bacterium.

Accordingly, the manufacturers are eager to develop functional probiotics able to modulate blood glucose.

SUMMARY OF THE INVENTION

The present invention provides food compositions and pharmaceutical compositions with lactic acid bacteria strains, which can modulate blood glucose and prevent from/treat diabetes mellitus.

In one embodiment, the food composition with lactic acid bacteria strains of the present invention comprises isolated GL-104 strain of *Lactobacillus reuteri* (CCTCC NO: M209138), isolated AP-32 strain of *Lactobacillus salivarius* subsp. *salicinius* (CCTCC NO: M2011127), and a physiologically-acceptable excipient or diluent. The abovementioned lactic acid bacteria strains are able to modulate blood glucose and are deposited in China Center For Type Culture Collection, Wuhan, China.

In another embodiment, the pharmaceutical composition with lactic acid bacteria strains of the present invention comprises isolated GL-104 strain of *Lactobacillus reuteri* (CCTCC NO: M209138), isolated AP-32 strain of *Lactobacillus salivarius* subsp. *salicinius* (CCTCC NO: M2011127), and a pharmaceutically-acceptable excipient or diluent. The abovementioned lactic acid bacteria strains are able to modulate blood glucose and are deposited in China Center For Type Culture Collection, Wuhan, China.

In yet another embodiment, the method for modulating blood glucose comprises administering to a user in need thereof an effective amount of a composition with lactic acid bacteria strains, wherein the composition includes isolated GL-104 strain of *Lactobacillus reuteri* fCCTCC NO: M209138); isolated AP-32 strain of *Lactobacillus salivarius* subsp. *salicinius* (CCTCC NO: M2011127), wherein the abovementioned lactic acid bacteria strains are able to modulate blood glucose and are deposited in China Center For Type Culture Collection; and a excipient or diluent.

Below, embodiments are described in detail in cooperation with the attached drawings to make easily understood the objectives, technical contents, characteristics and accomplishments of the present invention.

DESCRIPTION OF THE PREFERRED EMBODIMENTS

Figure 1:
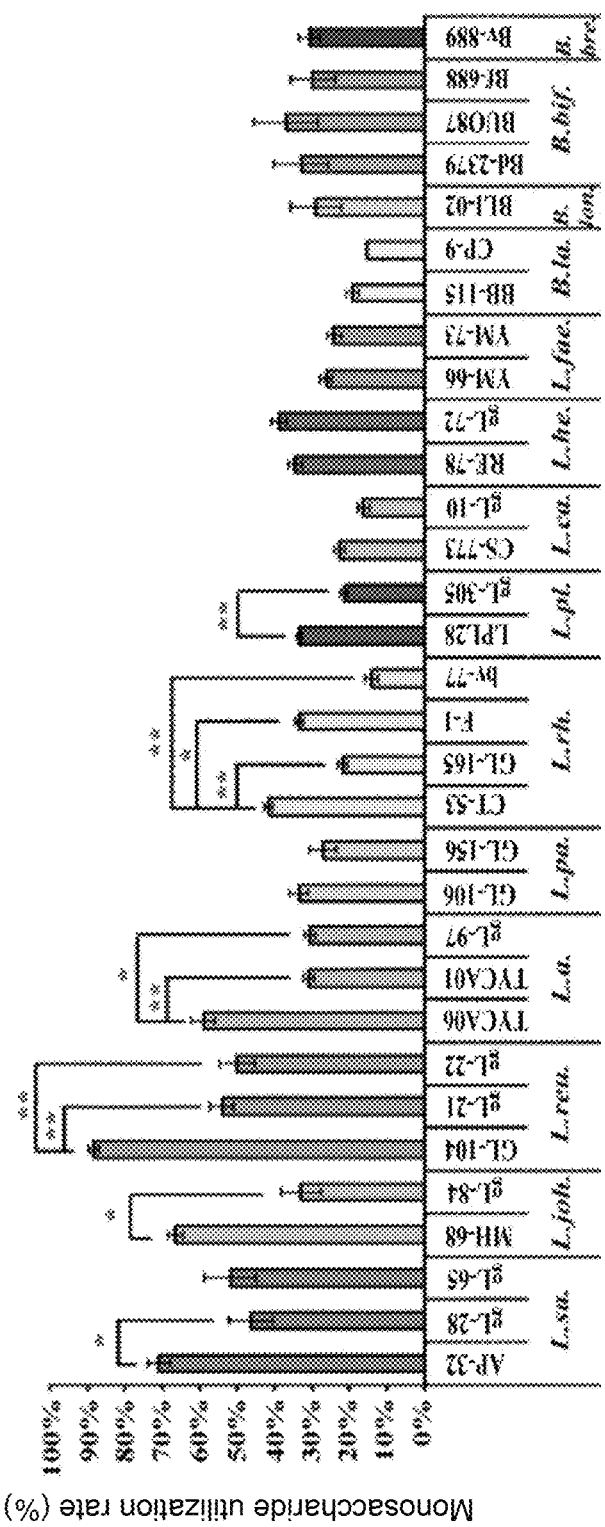
FIG. 1 is a histogram showing single-monosaccharide metabolic capabilities of a plurality of lactic acid bacteria strains.

The present invention will be described in detail with embodiments and attached drawings below. However, these embodiments are only to exemplify the present invention but not to limit the scope of the present invention. In addition to the embodiments described in the specification, the present invention also applies to other embodiments. Further, any modification, variation, or substitution, which can be easily made by the persons skilled in the art according to the embodiment of the present invention, is to be also included within the scope of the present invention, which is based on the claims stated below. Although many special details are provided herein to make the readers more fully understand the present invention, the present invention can still be practiced under a condition that these special details are partially or completely omitted. Besides, the elements or steps, which are well known by the persons skilled in the art, are not described herein lest the present invention be limited unnecessarily. Similar or identical elements are denoted with similar or identical symbols in the drawings. It should be noted: the drawings are only to depict the present invention schematically but not to show the real dimensions or quantities of the present invention. Besides, matterless details are not necessarily depicted in the drawings to achieve conciseness of the drawings.

The freeze-dried cultures of the lactic acid bacteria strains mentioned in the specification are respectively deposited in China Center For Type Culture Collection, Wuhan, China (Wuhan University, address: No. 299, Bayi Road, Wuchang District, Wuhan City, Hubei Province, China) and China General Microbiological Culture Collection Center, Beijing, China (address: Institute of Microbiology, Chinese Academy of Sciences, No. 1 Weat Beichen Road, Chaoyang District, Beijing 100101, China). The details thereof are listed in Table 1.

TABLE 1

Data of Deposited Lactic Acid Bacteria Strains

| Strain | Specie | Deposition No. | Deposition Date |
|---|---|---|---|
| GL-104 | Lactobacillus reuteri | CCTCC NO: M209138 | Aug. 7, 2009 |
| AP-32 | Lactobacillus salivarius subsp. salicinius | CCTCC NO: M2011127 | Apr. 10, 2011 |
| TYCA06 | Lactobacillus acidophilus | CGMCC No: 15210 | Jan. 15, 2018 |
| MH-68 | Lactobacillus johnsonii | CCTCC NO: M2011128 | Apr. 10, 2011 |

The four lactic acid bacteria strains listed in Table. 1, which are respectively the GL-104 strain of *Lactobacillus reuteri* (CCTCC NO: M209138), the AP-32 strain of *Lactobacillus salivarius* subsp. *salicinius* (CCTCC NO: M2011127), the TYCA06 strain of *Lactobacillus acidophilus* (CGMCC No: 15210), and the MH-68 strain of *Lactobacillus johnsonii* (CCTCC NO: M2011128), have physiological activity of modulating blood glucose. It should be understood by the persons skilled in the art: "modulating blood glucose" mentioned in the specification mainly means "decreasing the concentration of blood glucose to achieve the effect of preventing from/treating diabetes mellitus". Therefore, "physiological activity" mentioned in the specification is not limited to mean "modulating blood glucose", "controlling blood glucose", and "decreasing blood glucose" but means more than these phrases indicate.

In one embodiment, the present invention provides a food composition, which comprises isolated lactic acid bacteria strains, and a physiologically-acceptable excipient or diluent. The lactic acid bacteria strain is at least one isolated lactic acid bacteria strain selected from a group including a GL-104 strain of *Lactobacillus reuteri* (CCTCC NO: M209138), an AP-32 strain of *Lactobacillus salivarius* subsp. *salicinius* (CCTCC NO: M2011127), a TYCA06 strain of *Lactobacillus acidophilus* (CGMCC No: 15210), and an MH-68 strain of *Lactobacillus johnsonii* (CCTCC NO: M2011128). The abovementioned lactic acid bacteria strain may be an active one or an inactivated one. The abovementioned lactic acid bacteria strains are respectively deposited in China Center For Type Culture Collection and China General Microbiological Culture Collection Center.

In the embodiment of the food composition, the physiologically-acceptable excipient or diluent may be a food. The food may be but is not limited to be dairy food, tea, coffee, or a combination thereof. The dairy food may be fermented milk, yoghurt, cheese, or powdered milk. The number of the lactic acid bacteria strains may be over $10^6$ CFU (Colony-Forming Unit), preferably over $10^{10}$ CFU.

In one embodiment, the present invention provides a pharmaceutical composition, which comprises isolated lactic acid bacteria strains, and a pharmaceutically-acceptable excipient or diluent. The lactic acid bacteria strain is at least one isolated lactic acid bacteria strain selected from a group including a GL-104 strain of *Lactobacillus reuteri* (CCTCC NO: M209138), an AP-32 strain of *Lactobacillus salivarius* subsp. *salicinius* (CCTCC NO: M2011127), a TYCA06 strain of *Lactobacillus acidophilus* (CGMCC No: 15210), and an MH-68 strain of *Lactobacillus johnsonii* (CCTCC NO: M2011128). The abovementioned lactic acid bacteria strain may be an active one or an inactivated one. The abovementioned lactic acid bacteria strains are respectively deposited in China Center For Type Culture Collection and China General Microbiological Culture Collection Center.

In the embodiment of the pharmaceutical composition, the pharmaceutical composition may be in form of an oral dosage, such as a tablet, a capsule, a solution, or a powder. The number of the lactic acid bacteria strains may be over $10^6$ CFU (Colony-Forming Unit), preferably over $10^{10}$ CFU.

In one embodiment, the present invention provides a method for modulating blood glucose comprises administering to a user in need thereof an effective amount of a composition with lactic acid bacteria strains, which includes isolated lactic acid bacteria strain including a GL-104 strain of *Lactobacillus reuteri* (CCTCC NO: M209138), an AP-32 strain of *Lactobacillus salivarius* subsp. *salicinius* (CCTCC NO: M2011127), a TYCA06 strain of *Lactobacillus acidophilus* (CGMCC No: 15210), an MH-68 strain of *Lactobacillus johnsonii* (CCTCC NO: M2011128) or a combination thereof; and a excipient or diluent. For example, the composition with lactic acid bacteria strains may be the above-mentioned food composition or pharmaceutical composition.

It is learned via experiments: the tested lactic acid bacteria strains do not all have the same carbohydrate metabolism capability. The preliminarily-screened strains have significant difference in the influences on the related gene expression that intestinal cells absorb carbohydrate into blood circulation. Therefore, the Inventors only claim the four strains respectively deposited in China Center For Type Culture Collection and China General Microbiological Culture Collection Center, i.e. the GL-104 strain of *Lactobacillus reuteri* (CCTCC NO: M209138), the AP-32 strain of *Lactobacillus salivarius* subsp. *salicinius* (CCTCC NO: M2011127), the TYCA06 strain of *Lactobacillus acidophilus* (CGMCC No: 15210), and the MH-68 strain of *Lactobacillus johnsonii* (CCTCC NO: M2011128). The Inventors do not extensively claim all the lactic acid bacteria strains of the same species or all the strains tested by the Inventors.

Embodiment I: Morphologies and General Properties of the Strains of the Present Invention The taxonomic characteristics of the strains are identified with the 16S rDNA sequencing analysis and the API bacterial identification system. The morphologies and general properties of the strains are listed in Table. 2.

TABLE 2

Morphologies and General Properties of Lactic Acid Bacteria Strains of the Present Invention

| Strain | Morphology and characteristics |
|---|---|
| GL-104 strain of *Lactobacillus reuteri* | 1. While GL-104 is cultured in the MRS medium, the colony thereof has a shape of a solid circle and a color of white, the bodies of the bacteria each have a shape of a short rod, and the ends of the body are circular-shaped. The bodies of the bacteria often appear in single bodies. <br> 2. They are gram-positive bacilli, unlikely to generate spores, free of catalase, oxidase and motility, able to grow in aerobic and anaerobic environments, most suitable to grow at a temperature of 37 ± 1° C. They belong to a facultative hetero-fermentative strains and do not generate gas in glucose metabolism. |
| AP-32 strain of *Lactobacillus salivarius* | 1. While AP-32 is cultured in the MRS medium, the colony thereof has a shape of a solid circle and a color of white, the bodies of the bacteria each have a shape of a short rod, and the ends of the body are circular-shaped The bodies of the bacteria often appear in single bodies or in pairs of short chains. <br> 2. They are gram-positive bacilli, unlikely to generate spores, free of catalase, oxidase and motility, able to grow in aerobic and anaerobic environments, most suitable to grow at a temperature of 37 ± 1° C. They belong to a facultative hetero-fermentative strains and do not generate gas in glucose metabolism. |
| TYCA06 strain of *Lactobacillus acidophilus* | 1. While TYCA06 is cultured in the MRS medium, the colonies thereof are semitransparent and each have an irregular shape, the bodies of the bacteria each have a shape of a middle-size rod, and the ends of the body are circular-shaped. The bodies of the bacteria often appear in single bodies or short chains. <br> 2. They are gram-positive bacilli, unlikely to generate spores, free of catalase, oxidase and motility, able to grow in aerobic and anaerobic environments, most suitable to grow at a temperature of 37 ± 1° C. They belong to a facultative hetero-fermentative strains and do not generate gas in glucose metabolism. |
| MH-68 strain of *Lactobacillus johnsonii* | 1. While MH-68 is cultured in the MRS medium, the colonies thereof are semitransparent and each have an irregular shape, the bodies of the bacteria each have a shape of a middle-size rod, and the ends of the body are circular-shaped. The bodies of the bacteria often appear in single bodies or short chains. <br> 2. They are gram-positive bacilli, unlikely to generate spores, free of catalase, oxidase and motility, able to grow in aerobic and anaerobic |

TABLE 2-continued

Morphologies and General Properties of Lactic Acid Bacteria Strains of the Present Invention

| Strain | Morphology and characteristics |
|---|---|
| | environments, most suitable to grow at a temperature of 37 ± 1° C. They belong to a facultative hetero-fermentative strains and do not generate gas in glucose metabolism. |

Embodiment II: Using In-Vitro Experiments to Find out the Lactic Acid Bacteria Strains Favoring Monosaccharide Metabolism In this embodiment, the following lactic acid bacteria strains are used in the experiments: the AP-32 strain, gL-28 strain, and gL-65 strain of *Lactobacillus salivarius*; the MH-68 strain and gL-84 strain of *Lactobacillus johnsonii*; the GL-104 strain, gL-21 strain, and gL-22 strain of *Lactobacillus reuteri*; the TYCA06 strain, TYCA01 strain and gL-97 strain of *Lactobacillus acidophilus*; the GL-106 strain and GL-156 strain of *Lactobacillus paracasei*; the CT-53 strain, GL-165 strain, F-1 strain, and bv-77 strain of *Lactobacillus rhamnosus*; the LPL28 strain and gL-305 strain of *Lactobacillus plantarum*; the CS-773 strain and gL-10 strain of *Lactobacillus casei*; the RE-78 strain and gL-72 strain of *Lactobacillus helveticus*; the YM-66 strain and YM-73 strain of *Enterococcus faecium*; the BB-115 strain and CP-9 strain of *Bifidobacterium animalis* subsp. *lactis*; the BLI-02 strain of *Bifidobacterium longum*; the Bd-2379 strain, BUO87 strain, Bf-688 strain of *Bifidobacterium bifidum*; the Bv-889 strain of *Bifidobacterium breve*. The abovementioned strains are preserved in 50% glycerol at a temperature of −80° C. Before use, the abovementioned strains are activated twice with MRS broth (DIFCO) containing 0.05% cysteine at a temperature of 37° C. for 24 hours.

The abovementioned strains are respectively inoculated into culture medium in $1\times10^8$ CFU, wherein the culture medium is the MRS medium containing 60 mg/ml glucose, and wherein 0.05% cysteine is added to the culture medium for bifidobacteria. Next, the strain-inoculated mediums are cultured in incubators at a temperature of 37° C. for 20 hours. Next, the supernatants are collected, and the concentrations of reducing sugar are analyzed with the DNS reagent containing 27.4 mM 3,5-Dinitrosalicylic acid, 524 mM Sodium hydroxide and 879 mM Potassium sodium tartrate. Next, the monosaccharide utilization rates of the strains are worked out with the equation:

$$\frac{(\text{monosaccharide concentration in original culture medium (mg/ml)}) - (\text{reducing sugar concentration in supernatant (mg/ml)})}{(\text{monosaccharide concentration in original culture medium (mg/ml)})}$$

Refer to FIG. 1. The experimental results show that *Lactobacillus reuteri*, *Lactobacillus salivarius*, *Lactobacillus acidophilus*, and *Lactobacillus johnsonii* have higher monosaccharide metabolism capabilities than the other lactic acid bacteria and the bifidobacteria, wherein * expresses that p<0.05, which indicates that there is significant difference between both sides of comparison, and wherein ** expresses that p<0.01, which indicates that there is very significant difference between both sides of comparison.

Among these lactic acid bacteria, the GL-104 strain of *Lactobacillus reuteri*, AP-32 strain of *Lactobacillus salivarius* subsp. *salicinius*, TYCA06 strain of *Lactobacillus acidophilus*, and MH-68 strain of *Lactobacillus johnsonii* have the highest monosaccharide metabolism capabilities. It deserves to be mentioned: different strains of the same species have different blood glucose modulating capabilities. For example, among the three strains of *Lactobacillus reuteri*, the monosaccharide metabolism capability of the GL-104 strain is obviously higher than that of the gL-21 strain and gL-22 strain. Therefore, blood glucose modulating is not a species-specific ability but a strain-specific ability.

Embodiment III: Using In-Vitro Experiments to Find out the Lactic Acid Bacteria Strains Able to Metabolize Mixed Monosaccharides In this embodiment, the abovementioned strains are respectively inoculated into culture mediums in $1\times10^8$ CFU, wherein the culture medium is the MFG medium containing 20 mg/ml glucose, 20 mg/ml fructose and 20 mg/ml galactose. The strain-inoculated mediums are cultured in incubators at a temperature of 37° C. for 20 hours. Next, the supernatants are collected, and the concentrations of reducing sugar are analyzed with the DNS reagent containing 27.4 mM 3,5-Dinitrosalicylic acid, 524 mM Sodium hydroxide and 879 mM Potassium sodium tartrate. Next, the mixed-monosaccharide utilization rates of the strains are worked out.

Figure 2:
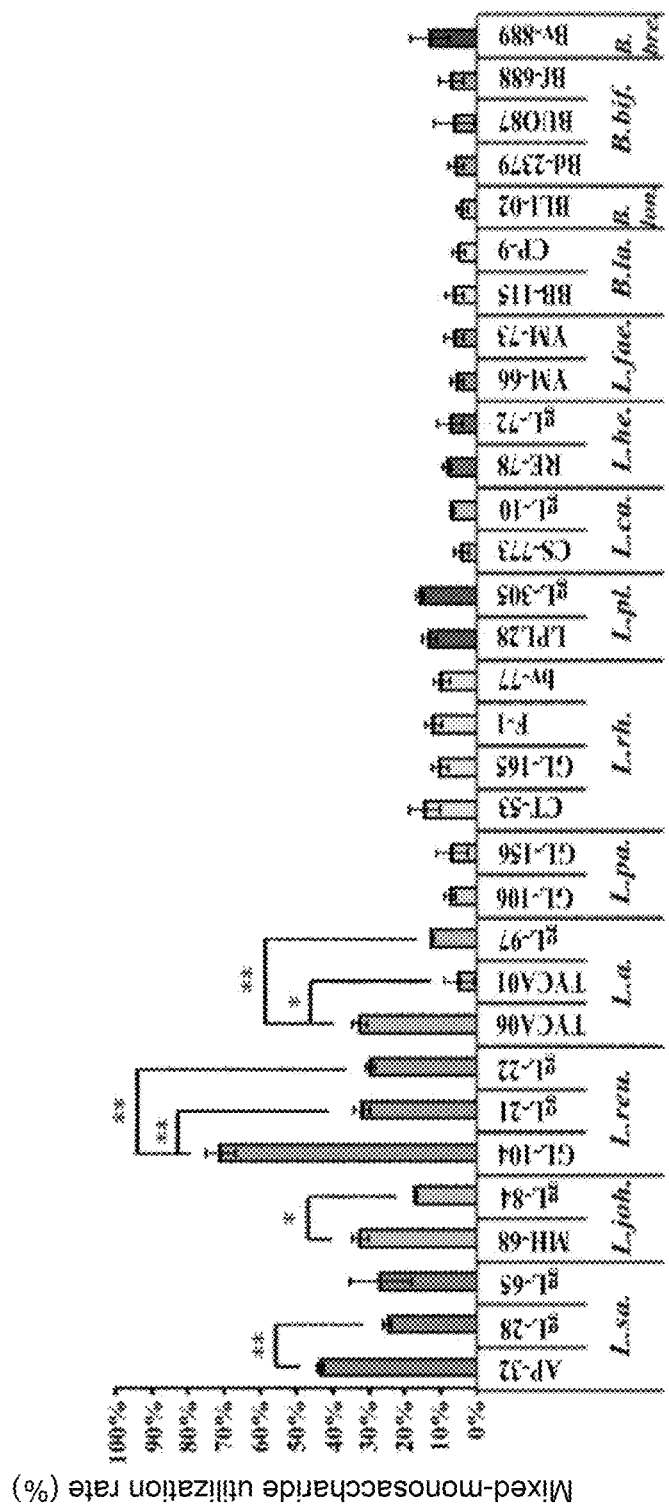
FIG. 2 is a histogram showing mixed-monosaccharide metabolic capabilities of a plurality of lactic acid bacteria strains.

Refer to FIG. 2. The experimental results show that *Lactobacillus reuteri*, *Lactobacillus salivarius*, *Lactobacillus johnsonii*, and *Lactobacillus acidophilus* have higher mixed-monosaccharide metabolism capabilities than the other lactic acid bacteria and the bifidobacteria, wherein * expresses that $p<0.05$, which indicates that there is significant difference between both sides of comparison, and wherein  expresses that $p<0.01$, which indicates that there is very significant difference between both sides of comparison. It is shown in FIG. 2**: among these lactic acid bacteria, the GL-104 strain of *Lactobacillus reuteri*, AP-32 strain of *Lactobacillus salivarius* subsp. *salicinius*, MH-68 strain of *Lactobacillus johnsonii* and TYCA06 strain of *Lactobacillus acidophilus* have the highest mixed-monosaccharide metabolism capabilities.

Food contains various kinds of carbohydrates. The carbohydrates are decomposed in the digestive tract into mainly glucose and other kinds of monosaccharides. It is easily understood: a strain having a high metabolism capability in a single monosaccharide (glucose) and mixed monosaccharides would have better blood glucose modulating effect.

Embodiment IV: Influences of the Lactic Acid Bacteria of the Present Invention on the Gene Expressions of SGLT1 and GLUT5

Rising of blood glucose is mainly owing to the fact that carbohydrates of food is digested by the intestinal tracts and absorbed into blood vessels by the intestinal mucosa. The sodium-glucose linked transporter 1 (SGLT1) and the glucose transporter 5 (GLUT5) are related with absorption of carbohydrates. SGLT1 is involved in the process that glucose is transported from the intestinal tract to the intestinal mucosa. GLUT5 is involved in the process that fructose is transported from the intestinal tract to the intestinal mucosa. Therefore, lowering the expression of SGLT1 would decelerate the absorption of glucose. In other words, transportation of sugar into blood circulation is decelerated, and rising of blood glucose is slowed down.

The human colon gland cancer cell line (Caco-2) is a superior in-vitro model for studying absorption and transportation of nutrient and medicine in the intestinal tracts. Caco-2 and lactic acid bacteria strains are co-cultured to learn the gene expressions of SGLT1 and GLUT5 in Caco-2 and thus grasp the influences of the lactic acid bacteria strains on blood glucose modulation. Thereby, we can find out the lactic acid strains able to lower blood glucose.

In this embodiment, Caco-2 is inoculated to the culture medium in a 6-well plate in $4\times10^5$ cells per well and cultured overnight. Next, lactic acid bacteria strains are added into the wells in $8\times10^8$ CFU per well and co-cultured with the culture medium for 20 hours. Next, collect the cells and extract the total RNA. Next, use a reverse transcriptase to reverse-transcript RNA into cDNA. Next, use the quantitative real time polymerase chain reaction (Q-PCR) to analyze the gene expressions of SGLT1 and GLUT5. In this embodiment, only Caco-2 is cultured in the control group; no lactic acid bacteria strain is co-cultured in the control group.

In this embodiment, the experiments use the following lactic acid bacteria strains: the GL-104 strain of *Lactobacillus reuteri*, AP-32 strain of *Lactobacillus salivarius* subsp. *salicinius*, MH-68 strain of *Lactobacillus johnsoni*, TYCA06 strain of *Lactobacillus acidophilus*, and F-1 strain of *Lactobacillus rhamnosus*. Each group of cells is cultured in an hMEM medium (a high-glucose culture medium containing 4.5 mg/ml glucose) and an hmMEM medium (a high-mixed-monosaccharide culture medium containing 1.5 mg/ml glucose, 1.5 mg/ml fructose and 1.5 mg/ml galactose) to study the influences of different lactic acid bacteria strains on the gene expressions of SGLT1 and GLUT5 in a single-monosaccharide environment and a mixed-monosaccharide environment. The experimental results are shown in FIGS. 3-8.

Figure 3:
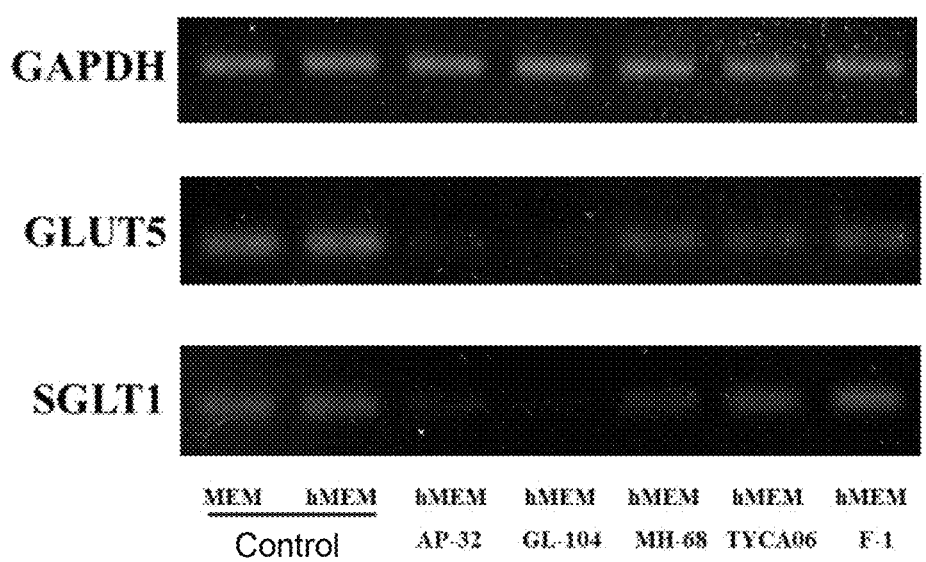
FIG. 3 shows an electrophoregram of the gene expressions of SGLT1 and GLUT5 while the human colon gland cancer cell line (Caco-2) and the lactic acid bacteria strains are co-cultured in a single-monosaccharide environment.
Figure 4:
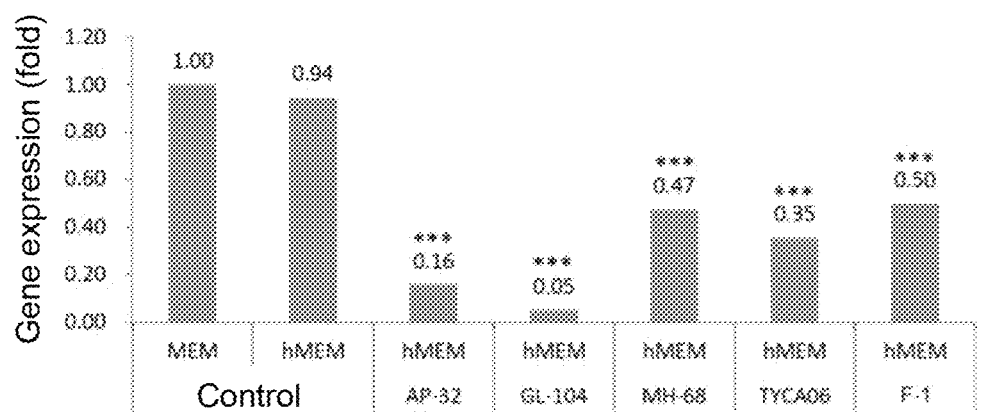
FIG. 4 is a histogram quantifying the gene expressions of GLUT5 in the electrophoregram of FIG. 3.
Figure 5:
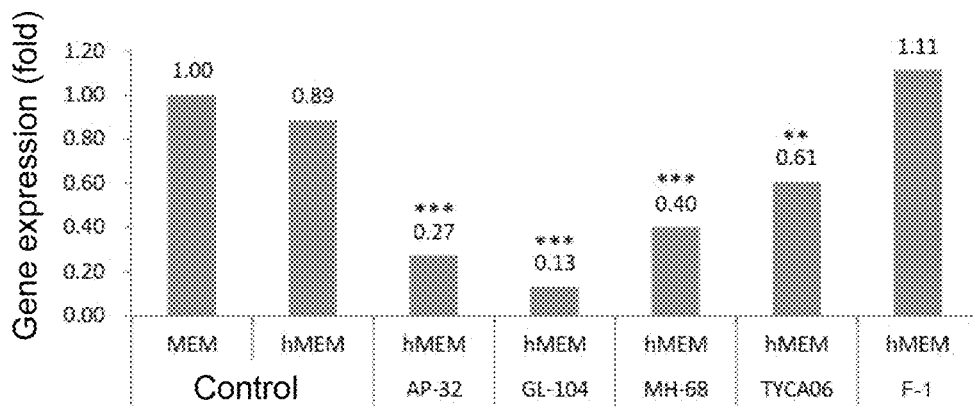
FIG. 5 is a histogram quantifying the gene expressions of SGLT1 in the electrophoregram of FIG. 3.

FIG. 3 shows an electrophoregram of the gene expressions of all the groups of cells in a single-monosaccharide environment, wherein the gene expression of glyceraldehyde 3-phosphate dehydrogenase (GAPDH) is used in the control groups. FIG. 4 shows a histogram quantifying the gene expressions of GLUT5 in the electrophoregram of FIG. 3, and FIG. 5 shows a histogram quantifying the gene expressions of SGLT1 in the electrophoregram of FIG. 3, wherein * expresses that $p<0.001$ and  expresses that $p<0.01$, both indicating significant statistic difference exists between two sides of comparison. It is found in FIGS. 3-5: in comparison with the control group MEM (glucose-containing medium), the GL-104 strain of *Lactobacillus reuteri*, AP-32 strain of *Lactobacillus salivarius* subsp. *salicinius*, MH-68 strain of *Lactobacillus johnsonii* and TYCA06 strain of *Lactobacillus acidophilus* of the present invention can inhibit the gene expressions of SGLT1 and GLUT5 in a single-monosaccharide environment. Therefore, the GL-104 strain of *Lactobacillus reuteri*, AP-32 strain of *Lactobacillus salivarius* subsp. *salicinius*, MH-68 strain of *Lactobacillus johnsonii* and TYCA06 strain of *Lactobacillus acidophilus* of the present invention have superior effect in inhibiting the gene expressions of SGLT1 and GLUT5 in a single-monosaccharide environment.

Figure 6:
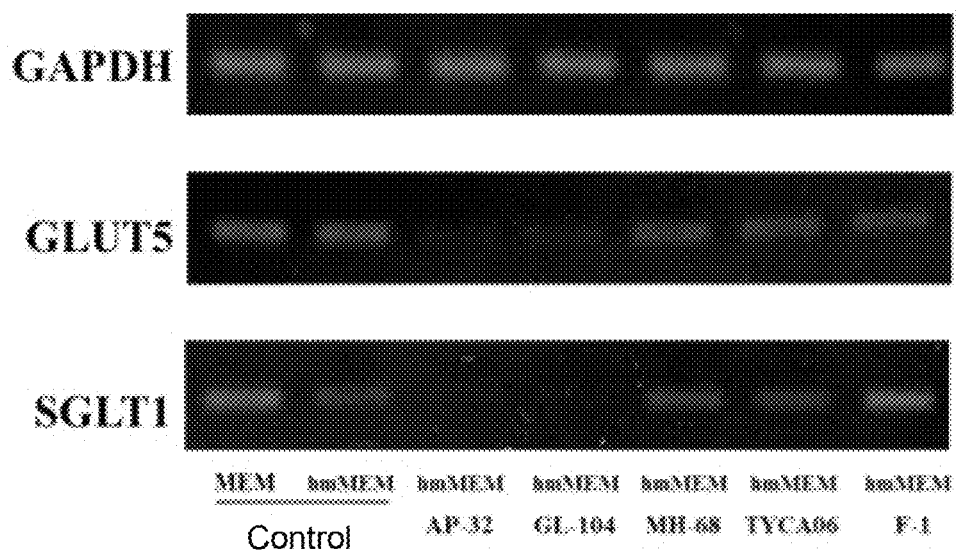
FIG. 6 shows an electrophoregram of the gene expressions of SGLT1 and GLUT5 while the human colon gland cancer cell line (Caco-2) and the lactic acid bacteria strains are co-cultured in a mixed-monosaccharide environment.
Figure 7:
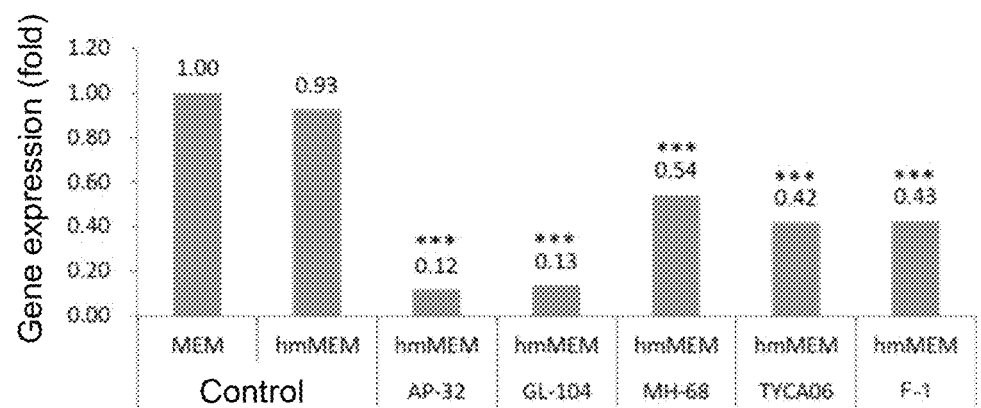
FIG. 7 is a histogram quantifying the gene expressions of GLUT5 in the electrophoregram of FIG. 6.
Figure 8:
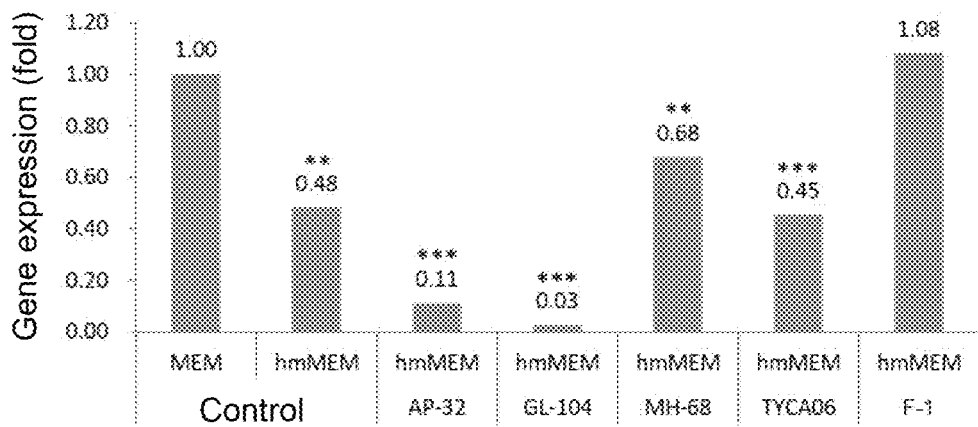
FIG. 8 is a histogram quantifying the gene expressions of SGLT1 in the electrophoregram of FIG. 6.

FIG. 6 shows an electrophoregram of the gene expressions of all the groups of cells in a mixed-monosaccharide environment, wherein the gene expression of glyceraldehyde 3-phosphate dehydrogenase (GAPDH) is used in the control groups. FIG. 7 shows a histogram quantifying the gene expressions of GLUT5 in the electrophoregram of FIG. 6, and FIG. 8 shows a histogram quantifying the gene expressions of SGLT1 in the electrophoregram of FIG. 6, wherein * expresses that p<0.001 and  expresses that p<0.01, both indicating significant statistic difference exists between two sides of comparison. It is found in FIGS. 6-8: in comparison with the control group MEM (glucose-containing medium), the GL-104 strain of *Lactobacillus reuteri*, AP-32 strain of *Lactobacillus salivarius* subsp. *salicinius*, MH-68 strain of *Lactobacillus johnsonii* and TYCA06 strain of *Lactobacillus acidophilus* of the present invention can inhibit the gene expressions of SGLT1 and GLUT5 in a mixed-monosaccharide environment. The GL-104 strain of *Lactobacillus reuteri*, AP-32 strain of *Lactobacillus salivarius* subsp. *salicinius*, MH-68 strain of *Lactobacillus johnsonii* and TYCA06 strain of *Lactobacillus acidophilus* of the present invention have superior effect in inhibiting the gene expressions of SGLT1 and GLUT5 in a mixed-monosaccharide environment.

It is learned from the abovementioned discussion: the GL-104 strain of *Lactobacillus reuteri*, AP-32 strain of *Lactobacillus salivarius* subsp. *salicinius*, MH-68 strain of *Lactobacillus johnsonii* and TYCA06 strain of *Lactobacillus acidophilus* of the present invention can inhibit the gene expressions of SGLT1 and GLUT5 and decelerate transportation of glucose and fructose into intestinal mucosa, whereby blood glucose is decreased. It should be further explained: in comparison with the F-1 strain of *Lactobacillus rhamnosus*, the GL-104 strain of *Lactobacillus reuteri*, AP-32 strain of *Lactobacillus salivarius* subsp. *salicinius*, MH-68 strain of *Lactobacillus johnsonii* and TYCA06 strain of *Lactobacillus acidophilus* of the present invention have relatively better effect of inhibiting the gene expressions of SGLT1 in an hMEM medium (high-glucose medium) and an hmMEM medium (high-mixed-monosaccharide medium), as shown in FIG. 5 and FIG. 8. Therefore, the lactic acid bacteria strains of the present invention can delay absorption of glucose and lower the rising rate of blood glucose.

In conclusion, the lactic acid bacteria strains of the present invention have superior monosaccharide metabolism capability, able to inhibit the gene expressions of SGLT1 and GLUT5 and lower the rising rate of blood glucose. In comparison with the conventional oral antidiabetic drugs, the food composition and pharmaceutical composition with strains of lactic acid bacteria of the present invention has fewer side effects to human bodies. Further, in comparison with the conventional invasive treatment methods, such as insulin injection, the food composition and pharmaceutical composition with strains of lactic acid bacteria of the present invention can significantly improve the quality of life for patients. Therefore, the present invention is favorable for prevention and treatment of diabetes.

The embodiments have been described above to demonstrate the technical thoughts and characteristics of the present invention to enable the persons skilled in the art to understand, make, and use the present invention. However, these embodiments are only to exemplify the present invention but not to limit the scope of the present invention. Any equivalent modification or variation according to the spirit of the present invention is to be also included by the scope of the present invention.

BIORESOURCE DEPOSITION

CCTCC NO: M209138, China Center For Type Culture Collection, Aug. 7, 2009
CCTCC NO: M2011127, China Center For Type Culture Collection, Apr. 10, 2011
CGMCC No: 15210, China General Microbiological Culture Collection Center, Jan. 15, 2018
CCTCC NO: M2011128, China Center For Type Culture Collection, Apr. 10, 2011

What is claimed is:

1. A method for modulating blood glucose, comprising: administering to a user in need thereof an effective amount of a composition with lactic acid bacteria strains, wherein the composition includes isolated GL-104 strain of *Lactobacillus reuteri* (CCTCC NO: M209138); isolated AP-32 strain of *Lactobacillus salivarius* subsp. *salicinius* (CCTCC NO: M2011127), wherein the GL-104 strain of *Lactobacillus reuteri* and the AP-32 strain of *Lactobacillus salivarius* subsp. *salicinius* are able to modulate blood glucose and are deposited in China Center For Type Culture Collection; and a excipient or diluent.

2. The method for modulating blood glucose according to claim 1, wherein the lactic acid bacteria strain is an active strain.

3. The method for modulating blood glucose according to claim 1, wherein the lactic acid bacteria strain is an inactivated strain.

4. The method for modulating blood glucose according to claim 1, wherein the excipient or diluent is physiologically-acceptable excipient or diluent.

5. The method for modulating blood glucose according to claim 1, wherein the excipient or diluent is a food.

6. The method for modulating blood glucose according to claim 5, wherein the food is fermented milk, yoghurt, cheese, powdered milk, tea, coffee, or a combination thereof.

7. The method for modulating blood glucose according to claim 1, wherein the excipient or diluent is pharmaceutically-acceptable excipient or diluent.

8. The method for modulating blood glucose according to claim 7, wherein the composition is in form of an oral dosage.

9. The method for modulating blood glucose according to claim 1, wherein the composition further comprises at least one of isolated TYCA06 strain of *Lactobacillus acidophilus* (CGMCC No: 15210) and isolated MH-68 strain of *Lactobacillus johnsonii* (CCTCC NO: M2011128), which are able to modulate blood glucose and are respectively deposited in China General Microbiological Culture Collection Center and China Center For Type Culture Collection.

* * * * *